(12) United States Patent
Rabin

(10) Patent No.: US 12,046,341 B2
(45) Date of Patent: Jul. 23, 2024

(54) METHODS AND SYSTEMS FOR ELECTRONICALLY ADJUSTING A DOSING PATTERN OF A PATIENT UNDERGOING A MEDICAL REGIMEN

(71) Applicant: Bradford Rabin, Palo Alto, CA (US)

(72) Inventor: Bradford Rabin, Palo Alto, CA (US)

(73) Assignee: Bradford Rabin, Palo Alto, CA (US)

( * ) Notice: Subject to any disclaimer, the term of this patent is extended or adjusted under 35 U.S.C. 154(b) by 0 days.

(21) Appl. No.: 17/494,185

(22) Filed: Oct. 5, 2021

(65) Prior Publication Data

US 2023/0107786 A1    Apr. 6, 2023

(51) Int. Cl.
| G16H 20/10 | (2018.01) |
| G16H 10/20 | (2018.01) |
| G16H 10/60 | (2018.01) |
| G16H 40/60 | (2018.01) |

(52) U.S. Cl.
CPC .............. *G16H 20/10* (2018.01); *G16H 10/20* (2018.01); *G16H 10/60* (2018.01); *G16H 40/60* (2018.01)

(58) Field of Classification Search
CPC ........ G16H 20/10; G16H 10/20; G16H 10/60; G16H 40/60
See application file for complete search history.

(56) References Cited

U.S. PATENT DOCUMENTS

| 6,267,116 B1 * | 7/2001 | McMichael ........ A61K 49/0004 600/300 |
| 7,056,890 B2 | 6/2006 | Najarian |
| 7,553,818 B2 | 6/2009 | Najarian |
| 7,659,256 B2 | 2/2010 | Najarian |
| 7,674,776 B2 | 3/2010 | Najarian |
| 8,071,557 B2 | 12/2011 | Najarian et al. |
| 8,580,298 B2 | 11/2013 | Najarian et al. |
| 8,580,299 B2 | 11/2013 | Najarian et al. |
| 9,805,163 B1 * | 10/2017 | Panch ..................... G16H 10/60 |
| 10,937,533 B1 * | 3/2021 | Wiser ......................... A61J 7/04 |
| 2005/0054942 A1 | 3/2005 | Melker et al. |
| 2008/0110792 A1 | 5/2008 | McKinney et al. |

(Continued)

FOREIGN PATENT DOCUMENTS

| WO | WO 2000/076493 | 12/2000 |
| WO | WO 2008/153632 | 12/2008 |

(Continued)

OTHER PUBLICATIONS

Blasiak, Agata, Jeffrey Khong, and Theodore Kee. "Curate. AI: optimizing personalized medicine with artificial intelligence." SLAS Technology: Translating Life Sciences Innovation 25.2 (2020): 95-105. (Year: 2020).*

(Continued)

*Primary Examiner* — Jesse P Frumkin
(74) *Attorney, Agent, or Firm* — Levine Bagade Han LLP

(57) ABSTRACT

A method for electronically adjusting a dosage pattern of a patient undergoing a medical regimen by providing the patient with an electronic interface to obtain survey results of a health survey to provide the patient with a dosage plan having a patient dosage amount and instructing the patient to follow the patient dosage plan over a second period of time to extend a duration of efficacy of the medical substance and maintain a safety profile of the medical substance.

20 Claims, 19 Drawing Sheets

(56) References Cited

U.S. PATENT DOCUMENTS

| | | | |
|---|---|---|---|
| 2009/0054372 A1 | 2/2009 | Goldsmith | |
| 2009/0076338 A1* | 3/2009 | Zdeblick | G16H 40/67 600/300 |
| 2010/0312580 A1* | 12/2010 | Tarassenko | G16H 40/67 707/758 |
| 2011/0059170 A1 | 3/2011 | Mckinney et al. | |
| 2011/0224196 A1 | 9/2011 | Wilson et al. | |
| 2013/0085772 A1* | 4/2013 | Gaweda | G16Z 99/00 705/2 |
| 2013/0179184 A1* | 7/2013 | Hurst | G16H 10/20 705/3 |
| 2014/0100829 A1* | 4/2014 | Mould | G06N 7/01 703/2 |
| 2014/0288944 A1 | 9/2014 | Miller et al. | |
| 2014/0294950 A1 | 10/2014 | Tam et al. | |
| 2015/0099801 A1 | 4/2015 | Day et al. | |
| 2015/0352062 A1* | 12/2015 | Shalon | A61K 31/137 514/654 |
| 2016/0300037 A1* | 10/2016 | Mould | G16H 20/17 |
| 2018/0140564 A1* | 5/2018 | Shalon | A61J 1/035 |
| 2018/0189458 A1* | 7/2018 | Shanbhag | G16H 20/10 |
| 2018/0232496 A1* | 8/2018 | Broselow | G16H 70/40 |
| 2019/0121935 A1* | 4/2019 | Ho | G16C 20/30 |
| 2019/0171962 A1* | 6/2019 | Mould | G16H 50/50 |
| 2019/0267143 A1* | 8/2019 | Sikander | G16H 70/20 |
| 2019/0326002 A1* | 10/2019 | Mould | G16H 10/60 |
| 2019/0333617 A1* | 10/2019 | Tutera | G16H 20/10 |
| 2019/0355459 A1* | 11/2019 | Li | G16H 50/20 |
| 2020/0108029 A1* | 4/2020 | Shalon | A61K 31/137 |
| 2020/0185099 A1* | 6/2020 | Britt | G16H 50/70 |
| 2020/0243180 A1* | 7/2020 | Wamburu | G16H 50/20 |
| 2020/0245925 A1* | 8/2020 | Inwald | G16H 30/20 |
| 2020/0321096 A1* | 10/2020 | Mould | G16H 50/20 |
| 2021/0065860 A1* | 3/2021 | Keenan | G06F 16/24578 |
| 2021/0110904 A1* | 4/2021 | Ellenby | G06F 21/32 |
| 2022/0051775 A1* | 2/2022 | Rao | A61K 31/475 |
| 2022/0406427 A1* | 12/2022 | Bayuzick | G16H 10/60 |

FOREIGN PATENT DOCUMENTS

| | | |
|---|---|---|
| WO | WO 2009/152189 | 12/2009 |
| WO | WO 2009/152190 | 12/2009 |
| WO | WO 2011/085256 | 7/2011 |
| WO | WO 2014/134477 | 9/2014 |
| WO | WO 2015/054353 | 4/2015 |

OTHER PUBLICATIONS

FDA Phentermine (FDA Phentermine open label, Jan. 20, 2012).
Kim et al., "Effects on weight reduction and safety of short-term phentermine administration in Korean obese people", Yonsei Medical Journal, 47(5):614-625, Oct. 2006.

* cited by examiner

What is your medication sensitivity (ranked 1-5)?

1 —————●———— 5
4) below average sensitivity
1 = traditional doses of medicine have smaller positive or negative effects
5 = small amounts of medicine have large positive or negative effects cancer, heart disease List your allergies to medicine.

List your current medication.
Medicine | Quantity | Time/day
Ibuprofen | 3 ▾ | 1 ▾
⊕

NEXT

Patient Health Questionnaire (PHQ-9)

| | None | Few | Majority | All |
|---|---|---|---|---|
| 1. | □ | □ | □ | □ |
| a. | □ | □ | □ | □ |
| b. | □ | □ | □ | □ |
| c. | □ | □ | □ | □ |
| d. | □ | □ | □ | □ |
| e. | □ | □ | □ | □ |
| f. | □ | □ | □ | □ |
| g. | □ | □ | □ | □ |
| h. | □ | □ | □ | □ |
| 2. | □ | □ | □ | □ |

NEXT

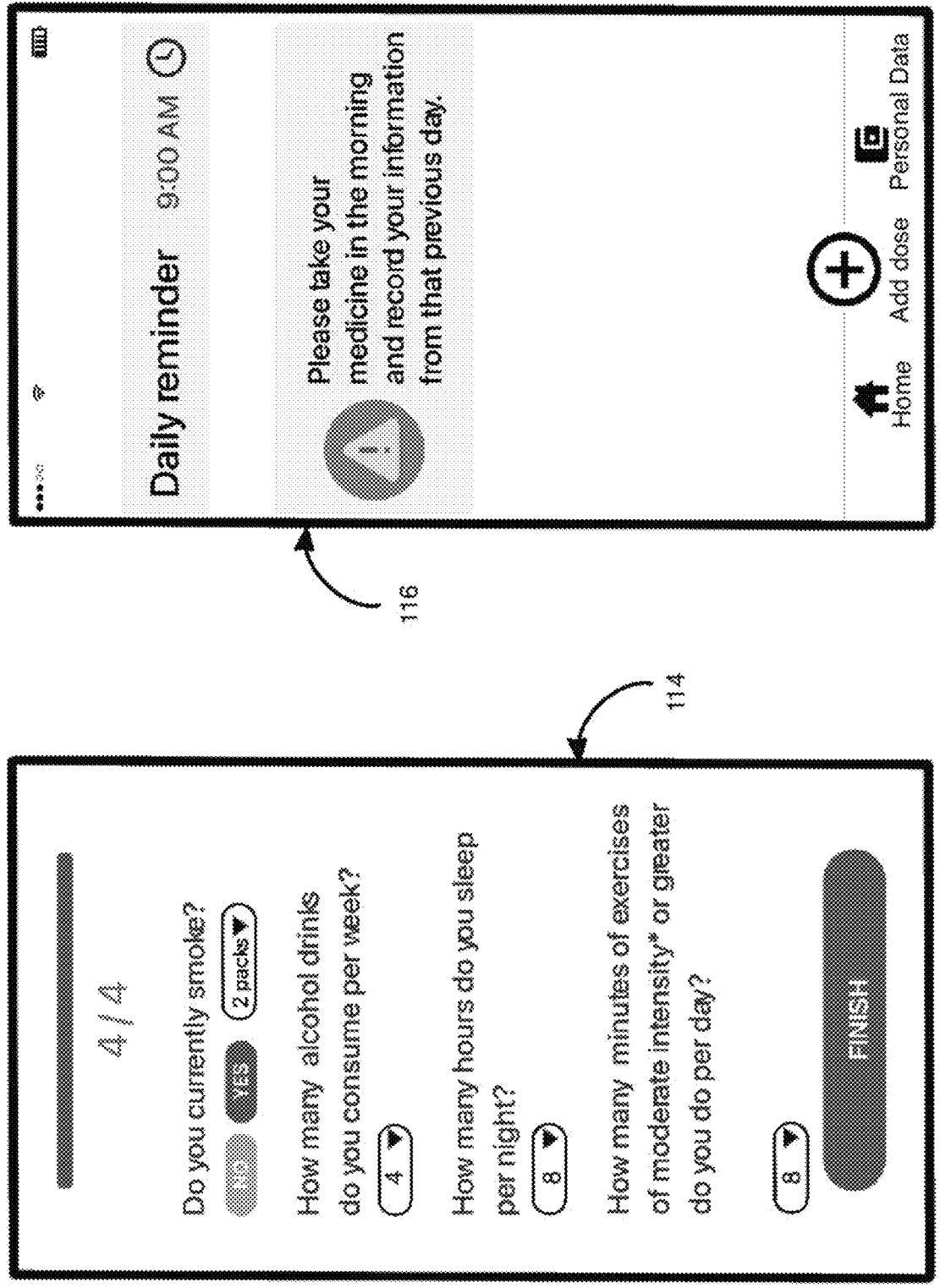

How long do you exercise at moderate intensity or greater?

0 min —————|———— 120 min

How long do you do mental exercises?

0 min |———————————— 120 min

What are your activities of daily living

- ☑ Eating 3 meals.
- ☑ Bathing and getting dressed.
- ◯ Managing a household though cleaning, removing trash, or doing laundry
- ☑ Social contact with friend or family member by phone or in person for > 10 minutes
- ◯ Attending job or pursuing a hobby or interest for > 4 hours per day
- ◯ Helping another person for > 30 minutes

NEXT

What is your water consumption?

( < 4 cups/d ) ( 4-7 cups/d ) ( > 7 cups/d )

What is your vegetable consumption?

( none ) ( 1-2 servings )
( 3-4 servings ) ( >5 servings )

What is your simple carbs consumption?

( none ) ( 1-2 servings )
( 3-4 servings ) ( >5 servings )

What is your sugar consumption?

( none ) ( 1-2 servings )
( 3-4 servings ) ( >5 servings )

NEXT

Patient Health Questionnaire (PHQ - 9)

1. Over the last 2 weeks, how often have you been bothered by any of the following problems?

| | Not at all | Several days | More than half the days | Nearly every day |
|---|---|---|---|---|
| a. Little interest or pleasure in doing things | ☐ | ☐ | ☐ | ☐ |
| b. Feeling down, depressed, or hopeless | ☐ | ☐ | ☐ | ☐ |
| c. Trouble falling/staying asleep, sleeping too much | ☐ | ☐ | ☐ | ☐ |
| d. Feeling tired or having little energy | ☐ | ☐ | ☐ | ☐ |
| e. Poor appetite or overeating | ☐ | ☐ | ☐ | ☐ |
| f. Feeling bad about yourself or that you are a failure or have let yourself or your family down | ☐ | ☐ | ☐ | ☐ |
| g. Trouble concentrating on things, such as reading the newspaper or watching television | ☐ | ☐ | ☐ | ☐ |
| h. Moving or speaking so slowly that other people could have noticed. Or the opposite, being so fidgety or restless that you have been moving around a lot more than usual. | ☐ | ☐ | ☐ | ☐ |
| i. Thoughts that you would be better off dead or of hurting yourself in some way. | ☐ | ☐ | ☐ | ☐ |

2. If you checked off any problem on this questionnaire so far, how difficult have these problems made it for you to do your work, take care of things at home, or get along with other people?

| Not difficult at all | Somewhat difficult | Very difficult | Extremely difficult |
|---|---|---|---|
| ☐ | ☐ | ☐ | ☐ |

FIG. 3

| Investigator | Length (weeks) | Dose (mg) | Phentermine weight loss (lbs) | Placebo weight loss (lbs) | Patients who completed |
|---|---|---|---|---|---|
| Kim[1] | 14 | 37 | 15.9 | 4.2 | 68 |
| Campell[2] | 12 | 30 | 8.1 | 2.2 | 66 |
| Truant[3] | 14 | 30 | 18.8 | 9 | 49 |
| Langlois[4] | 12 | 30 | 13.3 | 4.6 | 41 |
| Munro[5] | 12 | 37 | 20.1 | 9.8 | 42 |
| Average | | | 15.2 | 5.9 | |

FIG. 5A

| Pattern level | Purpose | Monday | Tuesday | Wednesday | Thursday | Friday | Saturday | Sunday |
|---|---|---|---|---|---|---|---|---|
| 6 | Weight loss | 35 | 35 | 0 | 0 | 35 | 0 | 35 |
| 5 | Weight loss | 15 | 15 | 0 | 0 | 15 | 0 | 15 |
| 4 | Weight loss | 10 | 10 | 0 | 0 | 10 | 0 | 10 |
| 3 | Maintenance | 15 | 0 | 0 | 15 | 0 | 0 | 0 |
| 2 | Maintenance | 7.5 | 0 | 0 | 7.5 | 0 | 0 | 0 |
| 1 | Maintenance | 0 | 0 | 0 | 0 | 0 | 0 | 0 |

* Values are in milligrams of active ingredient

FIG. 6A

| Pattern level | Purpose | Monday | Tuesday | Wednesday | Thursday | Friday | Saturday | Sunday |
|---|---|---|---|---|---|---|---|---|
| F | Weight loss | 37.5 | 37.5 | 0 | 0 | 37.5 | 0 | 37.5 |
| E | Weight loss | 37.5 | 0 | 0 | 37.5 | 0 | 0 | 0 |
| D | Weight loss | 15 | 15 | 0 | 0 | 15 | 0 | 10 |
| C | Maintenance | 15 | 0 | 0 | 15 | 0 | 0 | 0 |
| B | Maintenance | 0 | 15 | 0 | 0 | 0 | 0 | 0 |
| A | Maintenance | 0 | 0 | 0 | 0 | 0 | 0 | 0 |

* Values are in milligrams of active ingredient

FIG. 6B

|  | As disclosed | Munro Placebo | Munro Phentermine | Phentermine /placebo monthly cycle |
|---|---|---|---|---|
| Intent to treat (patients started) | 20 | 36 | 36 | 36 |
| Average starting weight (lb) | 207 | 203 | 207 | 214 |
| Dropped out during first 12 weeks | - | 11 | 19 | 14 |
| % drop out | 0% | 31% | 53% | 39% |
| 12 weeks average weight loss (lb) + | 22.75 | 8.34 | 13.00 | 15.46 |
| 36 weeks average weight loss (lb) *+ | 29.54 | 8.91 | 17.49 | 21.24 |
| Average dose (mg)/day during first 12w | 7.14 | - | 30.00 | 15.00 |

+ Using Munro weekly reported data for completers and non-complete reports at 0 weight loss
* not all patients in our study completed treatment. Reported is the average their latest weight

FIG. 9

METHODS AND SYSTEMS FOR ELECTRONICALLY ADJUSTING A DOSING PATTERN OF A PATIENT UNDERGOING A MEDICAL REGIMEN

CROSS-REFERENCE TO RELATED APPLICATIONS n/a

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

The current standard of medical care exposes patients to a uniform dose of medication on a daily basis as predicted by the body's breakdown of the drug, where the uniform dosage is determined by clinical studies involving large numbers of individuals. However, duration and efficacy of any drug are not unidimensional but instead multidimensional and complex. Drug efficacy can be determined by the dynamic interplay of the placebo response, drug-induced changes in the microbiome, and drug-induced changes in the GI, renal, and hepatic systems. Moreover, such efficacy can vary between individuals. Additionally, the effect of most drugs is tightly linked to their active metabolites and drug-related changes in gene expression. Lastly, drug-induced changes in receptor number and affinity and intracellular effectors with repeated drug exposure alter both responses to the administered drug as well as the body's endogenous compounds that act at these receptors.

Current trials intended to establish optimal drug dosing look at increases or decreases in daily dose but do not consider the rhythm and range of daily dosing that may be best suited to maintain drug efficacy, minimize drug withdrawal and dependence, avoid adverse effects, and in turn increase compliance.

A process of defining optimal drug dosing uses machine-learning to define the range within which one or more drugs can be fluctuated to optimize drug efficacy, minimize adverse effects, and defer tolerance. In a time when our understanding of the complex, dynamic interaction of the multiple systems that determine drug efficacy is limited, this novel approach leverages the wisdom and benefits of these systems before our scientific models have the sophistication to predict them.

There remains a need to increase an effectiveness or prolong a period of efficacy for one or more medicinal substances by interacting with and monitoring a patient on a repeated basis so that the effects of the medicinal substance can be extended where they otherwise would lose efficacy. Additionally, the methods described herein improve safety and avoid issues of tolerance and withdrawal that might otherwise be associated with the medicinal substance. This invention takes drugs with proven efficacy and safety that are limited by tolerance and extends their duration of efficacy while improving their safety profile and compliance.

BRIEF SUMMARY OF THE INVENTION

The methods and systems described herein are intended for electronically attending to a patient undergoing a medical regimen for increasing effectiveness of a medical substance taken during the medical regimen and to optimize efficacy of the medical substance while minimizing adverse effects and defer tolerance for the patient.

In one variation, the methods include providing an electronic interface to the patient after a first period of time during which the patient follows an existing dosing plan for a medicinal substance, the existing dosing plan having an existing dosing amount and an existing dosing cadence; assessing, using one or more processors of the electronic interface, at least one health survey containing a plurality of patient data regarding an effect of the medicinal substance on the patient; transmitting the plurality of patient data from the electronic interface to a server using a network; analyzing, using one or more processors of the server, the plurality of patient data to select a patient dosage plan from a database containing a plurality of pre-determined dosage plans stored on the server, where each pre-determined dosage plan in the plurality of pre-determined dosage plans is unique, where each pre-determined dosage plan includes a plurality of dosage amounts and a dosage cadence; where the plurality of dosage amounts includes at least a fractional dosage amount and a full dosage; and transmitting the patient dosage plan having a patient dosage amount from the server to the electronic interface to be displayed on an electronic display of the electronic interface, wherein the patient dosage plan instructs the patient to follow the patient dosage plan over a second period of time.

Variations of the method can include assessing at least one health survey from the patient that includes prompting the patient using the electronic interface with at least one health survey to allow the patient to provide the plurality of patient data, where the at least one health survey questionnaire includes a plurality of survey questions regarding the effect of the medicinal substance on the patient.

Variations of the method can also include assessing the at least one health survey further comprises receiving the at least one health survey containing the plurality of patient data from a personal electronic device configured to measure biologic or behavioral data from the patient.

Another variation of the method can include assessing the at least one health survey further comprises receiving, from a personal electronic device of the patient, a result from a test of a biologic sample from the patient to identify one or more biomarkers from the biologic sample.

Additional variations of the method can include any combination of health surveys that include one or more of patient questionnaires, data from electronic devices, and/or assessment of biological samples submitted by the patient.

Fractional dosage generally means that an individual will be assigned a dosage plan having a maximum dosage to be taken at a given time, where the fractional dosage is a partial amount of the maximum dosage. For example, a pre-determined dosage plan can include a maximum dosage or full dosage of 5 mg. The fractional dosage amounts can include any fraction/percentage of the full dosage such as: 0.5 mg (10%), 1 mg (20%), 2 mg (40%), 3 mg (60%), 4 mg (80%). Clearly, any fractional amount is within the scope of this disclosure. In some variations, the systems and methods will set a maximum dosage equal to a recommended starting dose, marketed amount, or usual recommended dose ("FDA Dosage") provided in the Dosage and Administration section of the labeling associated with a drug approved by the Food and Drug Administration ("FDA"). For example, a maximum dosage can be equivalent to the dosage form and administration provided by 21 CFR section 201.57. In most variations, the maximum dosage will not exceed the FDA Dosage. However, in additional variations of systems and methods the maximum dosage can exceed the FDA Dosage (e.g., for a clinical trial) or for substances that do not require FDA approval.

The electronic interface can comprise an app on a personal electronic device (e.g., a smart-phone, tablet, etc.), an internet site, or an electronic device solely provided for the interaction required for the method.

In one variation, the method includes a plurality of dosage amounts that includes a zero-dosage amount. In such cases, the patient may or may not be aware that they are ingesting a reduced or zero-dosage amount of the medical substance.

In an additional variation, the method and systems can further include providing the patient with a plurality of doses of the medical substance in an amount equal to the patient's dosage amount. For example, the patient can be provided with the medical substance already arranged in the dosage amounts determined by the analysis. As discussed herein, the patient may or may not be aware of the specific dosage amounts being ingested (e.g., a full dosage pill/tablet can look identical to a fractional or zero-dosage tablet).

In additional variations of the method and system, the patient dosage amount is obscured from the patient.

The survey questions can include at least one question related to an effectiveness of the medicinal substance on the patient. Alternatively, or in combination, the survey questions can include questions related to a change in behavioral practices of the patient during the first period of time.

The methods and systems described herein can further include analyzing the plurality of patient data to select the patient dosage plan further by applying a machine-learning algorithm to select the patient dosage plan from the database containing a plurality of pre-determined dosage plans.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

In another variation, the methods described herein can include methods of assisting weight loss in a patient by administering a drug, where the drug comprises an approved moderate marketed dose amount having a continuous administration period limit, the method comprising: providing a dose pattern of the drug to the patient, where the dose pattern comprises a dosage amount of the drug distributed in a plurality of dose units each having a varying amount of the drug, where at least one dose unit comprises a low dose of the drug that is below the approved moderate marketed dose amount; instructing the patient to administer the dose pattern over a period of time; receiving a feedback from the patient after the period of time, where the feedback is electronically reported by the patient and comprises an effect of the dose pattern on the patient; analyzing the feedback to revise the dose pattern, wherein analyzing the feedback comprises: reducing the dosage amount of the dose pattern if the feedback includes an adverse side effect of the drug; increasing the dosage amount of the dose pattern if the feedback indicates a hunger level is not decreasing or if the feedback indicates a patient's weight is not decreasing or not maintained; maintaining the dosage amount of the dose pattern if the feedback indicates the hunger level decreases, the patient's weight is decreasing or maintained, and a lack of the side effect of the drug; and providing a revised dose pattern of the drug to the patient and repeating the steps such that the dosage amount of the dose pattern is minimized to prevent building the patient's tolerance to the drug while extending weight loss to an effective period that is greater than the continuous administration period limit.

Additional methods can providing a dose pattern of the drug to the patient, where the dose pattern comprises a dosage amount of the drug distributed in a plurality of dose units each having a varying amount of the drug, where at least one dose unit comprises a low dose of the drug that is below the approved moderate marketed dose amount; instructing the patient to administer the dose pattern over a period of time; monitoring a feedback provided by the patient to produce a minimized effective active dose pattern to prevent a side effect of the drug and maintain efficiency of the drug results while minimizing the dosage amount by providing dose units comprising both the low dose with the approved moderate marketed dose amounts; and providing the minimized effective active dose pattern to the patient and repeating the steps, where the minimized effective active dose pattern minimizes the patient's exposure to the drug to prevent the patient from building a tolerance to the drug and allows the patient to continue the drug for a period beyond the continuous administration period while losing or maintaining weight.

This application is related to U.S. patent application Ser. No. 16/417,113 filed May 20, 2019, which is a continuation of U.S. patent application Ser. No. 15/877,029 filed Jan. 22, 2018, which is a continuation of U.S. patent application Ser. No. 14/827,207 filed Aug. 14, 2015, which is a continuation of PCT International Application No. PCT/US2014/019482 filed Feb. 28, 2014, which claims priority to U.S. Provisional Patent Application No. 61/770,838 filed Feb. 28, 2013, each of which is incorporated by reference herein in its entirety.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A to 2K illustrate examples of health survey questionaries that are provided to a patient via an electronic interface to allow the patient to provide patient data that can be analyzed for selection of a patient dosage plan.

FIG. 3 illustrates an example of a health survey questionnaire presented via an electronic interface where the screen is similar to that shown in FIG. 2D.

FIG. 5A is a table showing the results of various previously published clinical trials using phentermine.

FIG. 6A is a chart showing exemplary dose pattern levels of phentermine as described herein.

FIG. 6B is a chart showing another exemplary set of dose pattern levels of phentermine as described herein.

FIG. 9 is a chart comparing results of varying dosages of phentermine as described herein with results from a previously published clinical trial.

DETAILED DESCRIPTION OF THE INVENTION

Figure 1A:
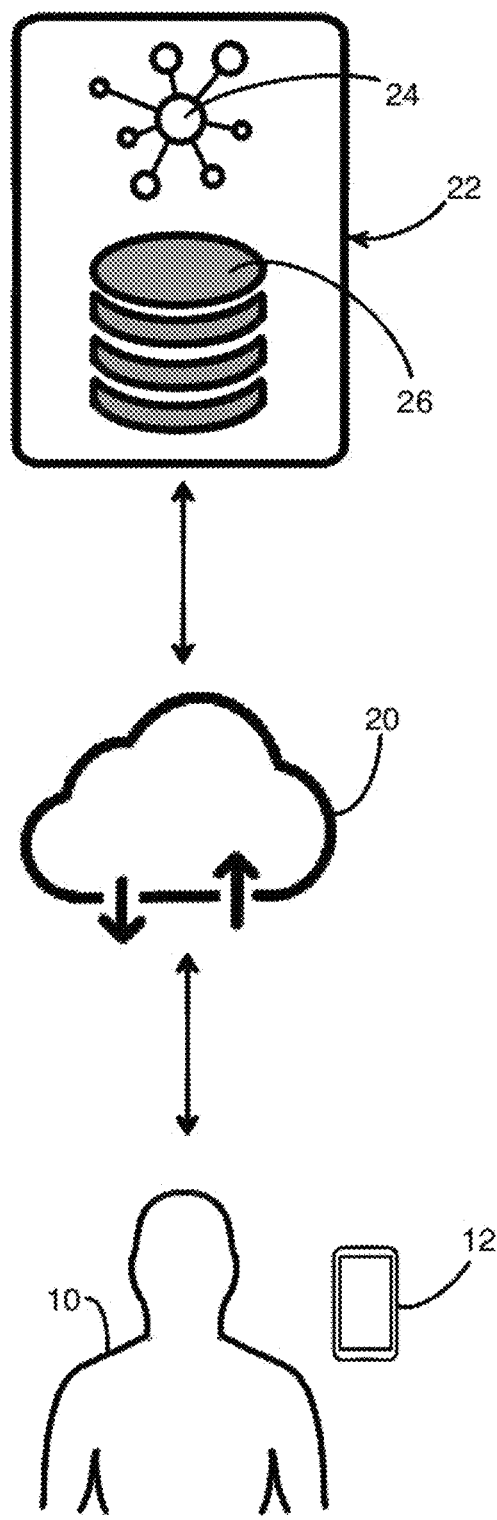
FIG. 1A illustrates an example of electronically attending to a patient undergoing a medical regimen to adjust a dosage of a medicinal substance based on interaction with the patient.

In general, described herein is a method of attending to a patient undergoing a medical regimen involving prescription of a dosing plan for one or more medicinal substances. Typically, the medical regimen is intended to treat a medical condition or to improve overall health of the patient. The method of attending to the patient is typically performed electronically, meaning that some or all of the interaction with the patient occurs remotely with the use of an electronic network to provide for real-time analysis of patient submitted data. The interaction with patients can occur via any number of modes of interaction. For example, the interaction can be active such as requiring the patient to answer surveys. The interaction can be passive interaction, where the patient wears (or uses) some type of electronic monitoring device such as a smart-watch, fitness or other health tracker that transmits data for assessment with little or no required patient action. The interaction can be biologic, such as where the interaction arises from an assessment of biomarkers from a patient's biologic sample.

One of the benefits of the methods described herein is to increase the effectiveness or prolong a period of efficacy for one or more medicinal substances. Additionally, the methods described herein improve safety, and avoid issues of tolerance and withdrawal that might otherwise be associated with the medicinal substance. This invention takes drugs with proven efficacy and safety that are limited, for example by tolerance or adverse effects, and extends their duration of efficacy while improving their safety profile and compliance.

One benefit of attending to the patient in the manner described is prolonging of the drug efficacy. Numerous classes of drugs, including weight loss drugs such as phentermine, quickly lose their efficacy. In a 4-week period of daily use phentermine loses its ability to control hunger and, in turn help patients lose weight. By extending the ability of phentermine to control hunger, this therapeutic approach prevents rapid development of tolerance and allows the efficacy to be maintained indefinitely. The present disclosure allows for the personalization of dosing to adjust for an individual's unique biology, the intraday variability response to medication given changes that may occur to an individual over time, and the behavior factors that influence this variability (e.g., the changes in behaviors required to reduce a dosage of the substance.)

Another benefit of the methods described herein minimizes drug exposure and decreases adverse effects. Generally, at higher doses, drugs have more adverse effects. The avoidance of tolerance decreases dose escalation. Rhythmic administration of drugs (alternating traditional doses with lower than traditional doses) takes into account the impact of dosing and rhythm of administration on the many levers in addition to drug breakdown that impacts adverse effects. Repeated daily dosing impacts the concentrations of metabolites, the regulation of DNA transcription, and efficiency of drug metabolism from GI tract to kidney and liver that may elevate the risk of adverse effects.

An additional benefit of this approach is the prevention or downmodulation of withdrawal which promotes unnecessary, extended and risky long-term use of drugs such as pain medications, anti-anxiety medications, and sleep medications. Patients using pain medications quickly build up tolerance and find that they are not deriving clinically significant benefits from the pain or sleeping medication, but it is difficult to stop these medicines because of withdrawal. This is thought to play a major role in propelling the long-term use of opiates and increasing the myriad of adverse effects seen with this class of drugs.

FIG. 1A illustrates an example of electronically attending to a patient undergoing a medical regimen to adjust a dosage of a medicinal substance based on interaction with the patient. As shown, the individual 10 uses an electronic interface 12 that is patient-based to interact with instructions from a caregiver or server 22. The electronic interface 12 can comprise a personal electronic device such as a phone, tablet, smart-watch, etc. Alternatively, the interaction can take place using a computer or customized device intended to interface with a server 22. The server 22 includes a database 26 that contains dosage plans as well as dosage schedules (i.e., a dosage cadence) for the patient to follow based on input from the patient. The database can also include a patient specific portion to maintain historical information of each patient such as previous dosing patterns, personal history, etc. The server 24 can include any additional processor or machine-learning algorithms that take into account the impact of dosing amounts and/or dosage cadence to provide updated guidance for the patient.

The interaction between the individual 10 and server can occur via a network 20 that is cloud based or via a direct/private network between the electronic interface 12 and server 22. As discussed below, the patient 10 can either be currently following an existing dosing plan for a medicinal substance. Alternatively, the patient can use the system to obtain an initial dosing plan.

The patient 10 is prompted to use the electronic interface to provide using at least one health survey questionnaire to allow the patient to provide a plurality of patient data, where the health survey questionnaire includes a plurality of survey questions regarding an effect of the medicinal substance on the patient. The results of the health survey, which comprise a plurality of patient data are transmitted to the server (either via a network or directly) where the plurality of patient data can be analyzed to select a patient dosage plan from a database containing a plurality of pre-determined dosage plans stored on the server as discussed in further detail below. In one variation of the method and system, each pre-determined dosage plan in the plurality of pre-determined dosage plans is unique, where each pre-determined dosage plan includes a plurality of dosage amounts and a dosage cadence (e.g., a time-based pattern that the patient follows in taking the medicine). In an additional variation of the methods and systems, the plurality of dosage amounts ranges includes at least a fractional dosage amount and a full dosage. The patient then receives the updated dosage plan and with instructions for the patient to follow the patient dosage plan over a second period of time.

Figure 1B:
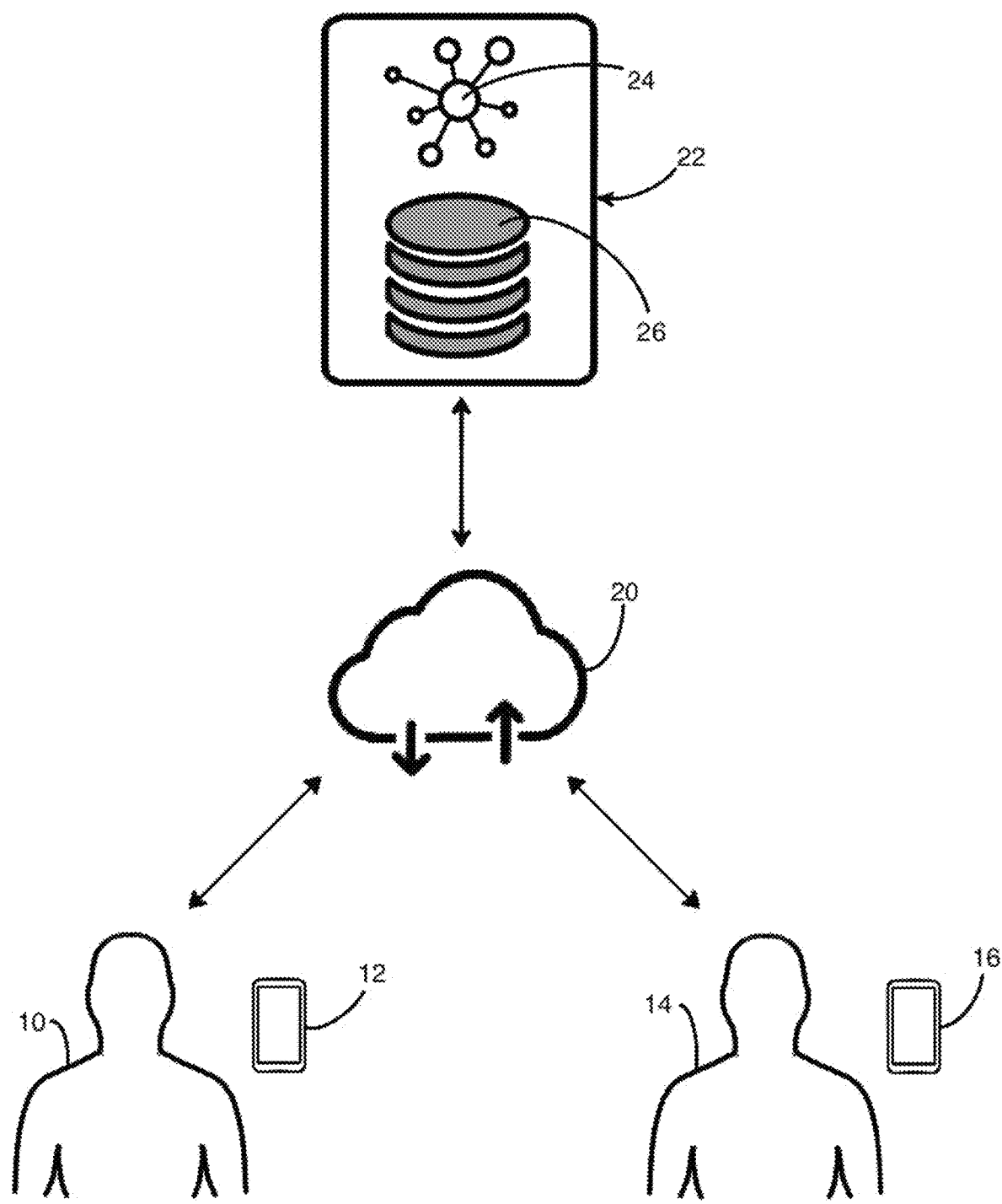
FIG. 1B illustrates as an example of the method and system providing customized treatment for a number of different individuals.

FIG. 1B illustrates as an example of the method and system providing customized treatment for a number of different individuals 10, 12. In practice, the system can interact with one or more individuals for creating or adjusting a medical regimen as described herein. The data and/or learning from each individual can be used to adjust the medical regimen for future and/or current patients.

While FIG. 1B and the following figures illustrate the use of health survey questionnaires for analysis to provide the patient with a patient dosage plan, additional variations of the invention can include assessing at least one health survey question from the patient by receiving the plurality of patient data from a personal electronic device configured to measure biologic or behavioral data from the patient. In this manner the patient submission of patient data can be purely passive.

Another variation of the method can include assessing at least one health survey question from the patient by receiving a biologic sample from the patient to identify one or more biomarkers from the biologic sample. While this method requires submission of a biologic component, it is partially passive since the patient is only submitting a biologic sample. Moreover, the patient can submit the results of the test of a biologic sample via the device 12/13 rather than submitting the actual sample.

In any case, any number of variations of the method include any combination of health surveys that include one or more of patient questionnaires, data from electronic devices, and/or assessment of biological samples submitted by the patient.

FIGS. 2A to 2K illustrate examples of health survey questionaries that are provided to a patient via an electronic interface to allow the patient to provide patient data that can be analyzed for selection of a patient dosage plan. The questions and data inputs provided in FIGS. 2A to 2K are intended for exemplary purposes. Any number of additional questions can be included. Moreover, any questions shown in the figures can be omitted as needed.

Figures 2A, 2B:
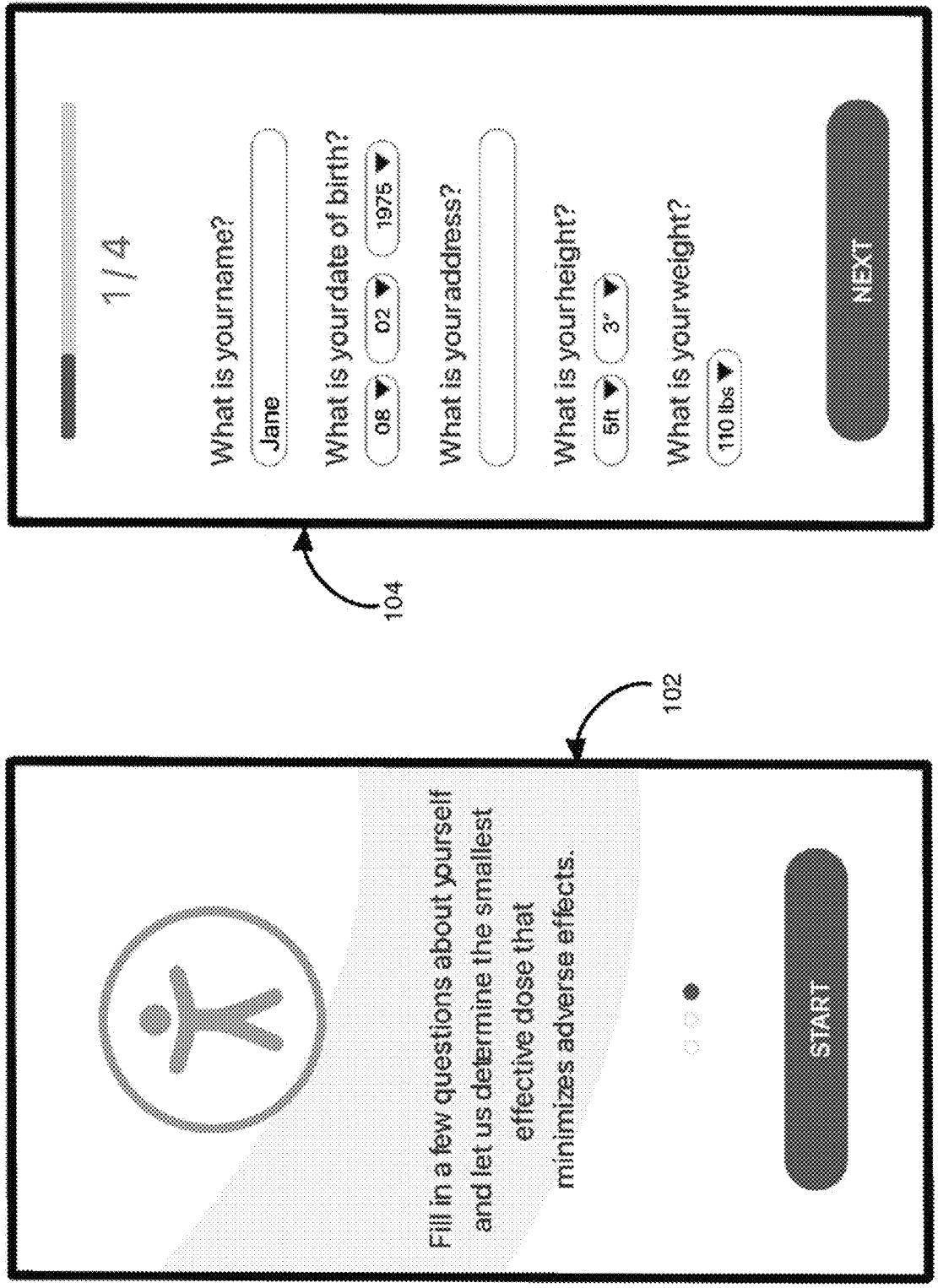
Figures 2G, 2H:
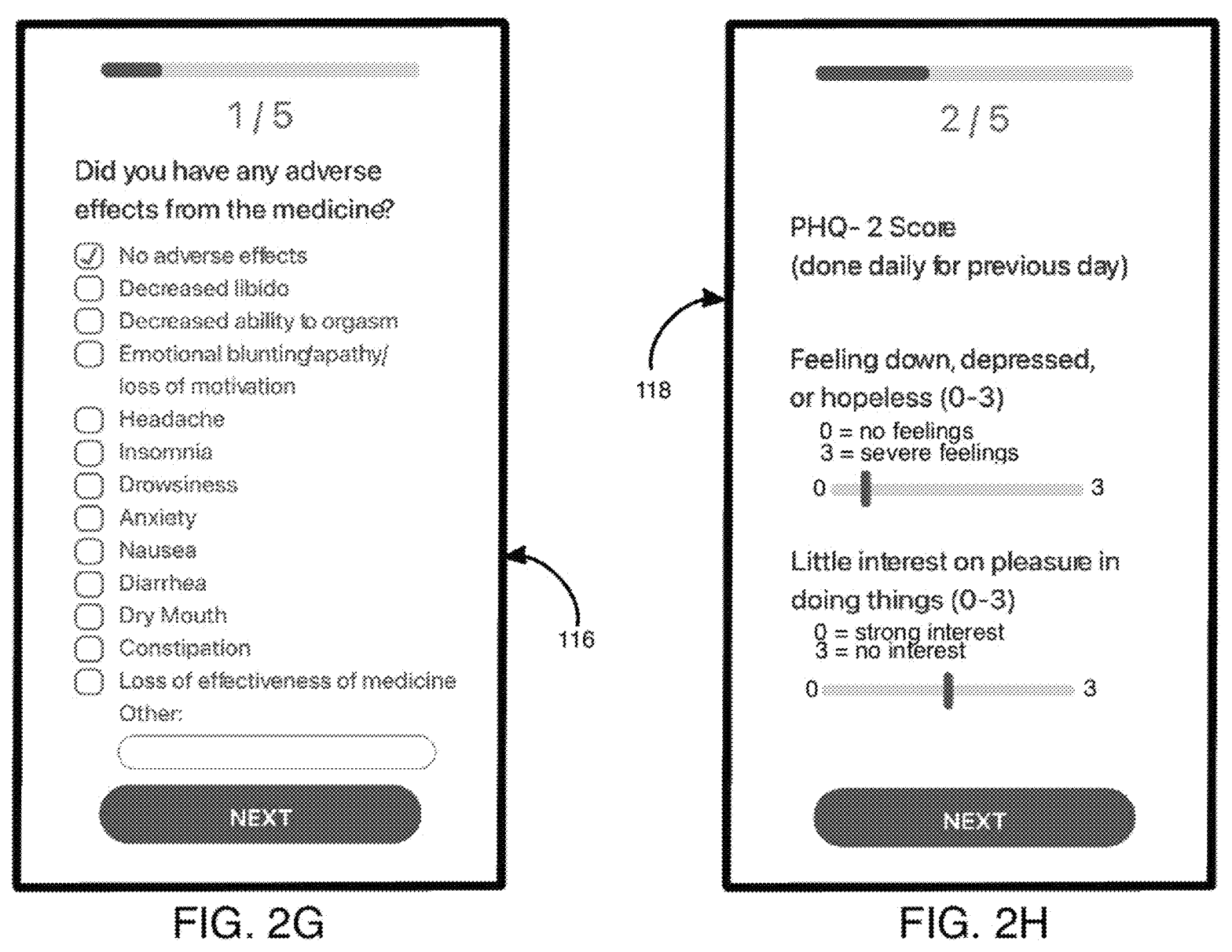
Figure 2K:
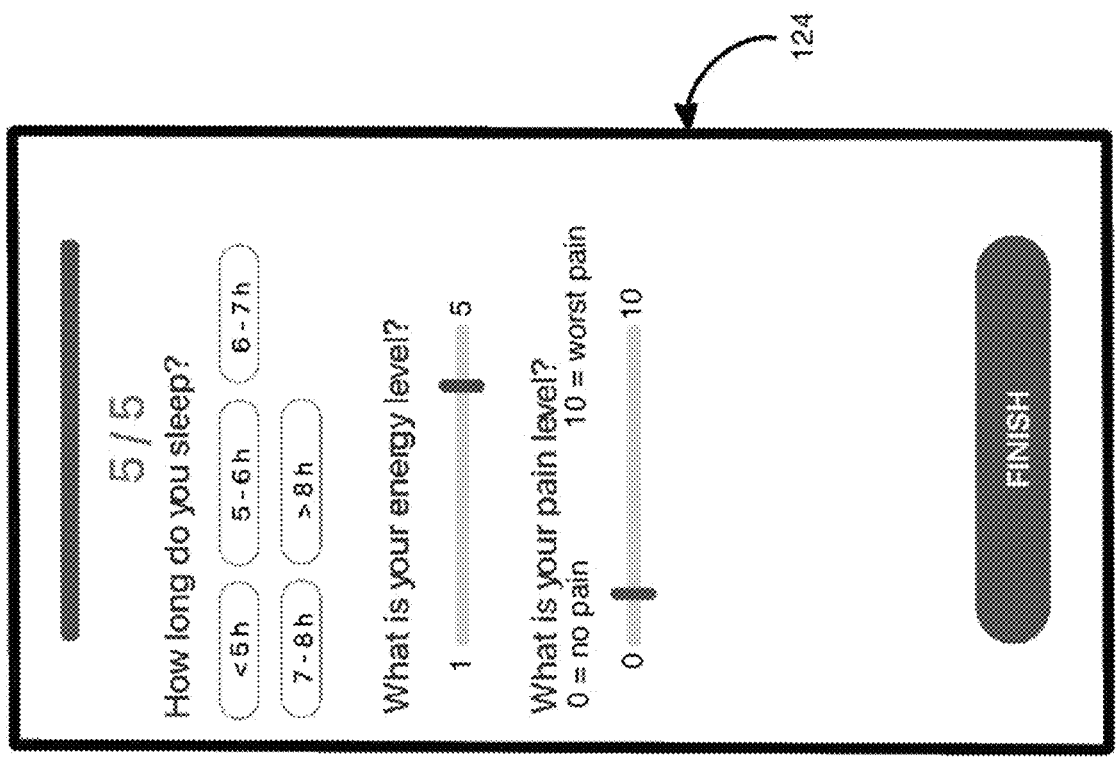

FIG. 2A illustrates an initial screen 102 of the electronic interface where the screen 102 displays background information related to the health survey questionnaire. FIG. 2B illustrates survey questions for the health survey questionnaire that is focused on background information of the patient. Such information can be used to verify the patient's identity or as an initial step in building a patient's profile. FIG. 2C illustrates a screen 106 of the electronic interface with survey questions related to a medical history of the patient as well as current medication schedules. The current medication schedules can be medications taken in addition to the medical substances being taken for the medical regimen of the current method. Alternatively, the current medication can include the medicinal substances being adjusted during the course of the medical regimen.

FIG. 2D shows a screen 107 of the electronic interface with one or more questions (illustrated by the boxes in area 108) comprising a personal-health questionnaire, where the questions are intended to gauge the effectiveness of the current medicinal dosage and dosing cadence. As shown, the personal health survey questionnaire can be identified (e.g., screen 107 in FIG. 2D is marked as "PHQ-9"). Such questions will be specific to the outcome of the medical regimen and the patient can assign a rating/rank/score to the questions in region 109. For example, various medical conditions that can be addressed using the methods and system described herein, include but are not limited to, obesity treatment, attention deficit disorder/hyperactivity, depression, anxiety, pain management (either opiate management or non-opioid medication), blood pressure management, gastro-intestinal issues, nausea, etc. Each medical regimen can provide survey questions 108 that are specific to the desired outcome of the treatment.

FIG. 2E shows an additional screen 114 from the electronic interface that prompts the patient to provide patient data relating to everyday activities or other information that is helpful to adjust a dosing plan for that individual. The screen 114 shown in FIG. 2E is for purposes of illustration where the questions relating to background or other information can be adjusted based on a number of factors that could potentially be relevant to adjusting of a dosing plan. FIG. 2F shows an example of the electronic interface providing a screen 116 to remind the patient to take a particular action, such as, taking the medication and recording information.

FIGS. 2G and 2H show additional screens 116, 118 for the electronic interface that prompts a patient to provide patient data relating to potential adverse effects of the medicine. As shown in FIG. 2G, the patient can choose any number of side effects associated with the medication. Alternatively, or in addition, FIG. 2H illustrates a screen 118 having an additional personal health survey questionnaire marked as "PHQ-2" (which provides a drug efficacy scale) where the patient can rate/rank/score potential side effects. Screen 118 also shows exemplary scores that can be assigned by the patient to allow for assessing the patient's present condition. In the illustrated example, the electronic interface displays personal health survey questionnaire (shown as PHQ-2) and prompts the patient to rate each question with a score/rank/ rating of zero to three. The patient's answers are submitted electronically to the server upon submission by the patient, where such data can be screened and used to select the patient's revised dosage plan. In this example, the potential PHQ-2 score can range from 0-6. The system can identify a certain score (e.g., 3 and above) as being indicative of a major depressive disorder. The system can alert a healthcare provider to directly contact the patient, as well as provide additional screening questions to further evaluate the patient or to apply, diagnostic instruments, or a direct interview to determine whether they meet criteria for a depressive disorder. Furthermore, each patient can have a unique score that indicates action should be taken. Such a personalized score can be assigned by a caregiver or through machine that, through the analysis of historical data, groups patients within certain subgroups. The server 22 can comprise a fully automated system that requires no human interaction with the analysis. Alternatively, or in combination, variations of the methods and systems include human interaction and/or supervision of the data received and transmitted to/from the patient. In an additional variation, the data gathering/transmission can be automated while the analysis is performed by a healthcare professional.

FIGS. 2I and 2J show additional screens 120, 122 and 124 from the electronic interface that prompts the patient to provide patient data relating to activities or other information that might be particularly applicable to side effects of the medication. Clearly, these screens 120, 122 and 124 can be combined with other background questions disclosed above.

FIG. 3 illustrates an example of a health survey questionnaire presented via an electronic interface where the screen 130 is similar to that shown in FIG. 2D. In this example, questions 108 are shown in association with various degrees of responses 131, 132, 133, 134. This interface allows the patient to assign a rating/score to each question based on the degree of the response. For example, the responses can be scored as follows: 131=1, 132=2, 133=3, 134=4. Clearly, any score can be assigned to the degree of the response 131, 132, 133, 134.

Variations of the method and systems described herein can use any combination of the screens and health survey questionnaires discussed above. In some variations, the patient does not enter any historical or personal data and is only prompted with one or more health survey questionnaires. In additional variations, a patient encounters a number of health survey questionnaires based upon the answer to an initial questionnaire. For example, if the patient's questions indicate that the dosage plan is effective with minimal side effects, then there is no need to adjust the dosage plan and no need to prompt the patient with additional health survey questionnaires. In addition, the methods and system can establish differentiated periods to further assist the patient. For example, for new patients, an initial period (e.g., 2 or 3 weeks) can be established as a first learning period. Then, the patient can enter a second learning period, where the system and methods collect and integrates the patient's personal data via the electronic interface to further refine optimal dosing and to coach the patient to increase lifestyle practices that will minimize their medication needs.

As noted above, the patient transmits the data to a server where the results of the health survey questionnaires are analyzed. This process can occur at any time period as required. For example, submission and analysis of the health survey questionnaire can occur daily, on a weekly basis, on a monthly basis, or over a pre-determined time frame (e.g., submission and analysis at weeks 2, 4, 6, and 8).

After a patient transmits the patient data to the server, the server analyzes the data to select a patient dosage plan from a database containing any number of pre-determined dosage plans that is associated with a specific score/rating from the submitted health survey questionnaire(s).

Figure 4A:
FIGS. 4A to 4E illustrate variations of a plurality of pre-determined dosage plans that can be stored on the server/database.

FIG. 4A illustrates one example of a plurality of pre-determined dosage plans 142 that can be stored on the server. As shown, each pre-determined dosage plan (A1 to A5) in the plurality of pre-determined dosage plans 142 is given the dosage amount per dose. However, variations of dosage plans can vary based on the dosage cadence (i.e., the schedule for taking each dose). FIG. 4A shows the dosage plans expressed as a fraction of the Full Dosage Segments shown to be ⅕. Which means that a standard dosage for a particular medicine being administered is to be given in fifths. For example, for a given medicinal substance that is administered in 20 mg, the dosage plan of A1 (5, 5, 2, 2, 5, 2, 5) would comprise individual dosages of 20 mg (5/5), 20 mg (5/5), 8 mg (⅖), 8 mg (⅖), 20 mg (5/5), 8 mg (⅖) and 20 mg (5/5). For example, for a given medicinal substance that is administered in 20 mg, the dosage plan of A5 varies between 4 mg (⅕) and 0 mg (0/5). In one example, it was found that the dosage plans 142 of FIG. 4A were useful to designate for varying levels of dosing patterns. For example, the does plans corresponded as follows: A1—high dose pattern, A2—high/mid level dose pattern, A3—mid level dose pattern, A4—low level dose pattern, A5—micro level dose pattern.

Figure 4B:

FIG. 4B illustrates a variation of expressing an exemplary dosage plan 144 in terms of percentages rather than segments. Regardless, the dosage plans vary the dosage amounts of a standard dose of medicinal substance to make the medicinal substance more effective or prolong the period of efficacy, improve safety, and avoid issues of tolerance and withdrawal.

Figure 4C:
Figure 4D:

In some variations, the patient is made aware of the varying dosage amounts. However, in alternate variations of the method and systems described herein, it may be desired to prevent the patient from observing the varying dosage amounts. FIGS. 4C and 4D illustrate the dosage plans 142, 144 of 4A and 4B respectively, but where the patient only observes a dosage identifier (e.g., D1 to D6) that corresponds to a dosage amount. In such a case, the actual doses of the medicinal substance are provided to the patient marked as D1 to D6. In such cases, each dosage amount (D1 to D6) looks the same but the varying dosage amount is not apparent to the patient.

Figure 4E:

FIG. 4E illustrates an additional example of a plurality of dosage plans 146 where the dosage plan C1 comprises two doses (⅖ and 5/5), where each dose is delivered daily and then the dosing repeats. Plans C2 to C4 comprises the same doses (5/5, ⅖, 0/5) but the dosing cadence changes from 4-hour, 8-hour, or daily and then the dosing repeats.

As noted above, the patient data submitted to the server is analyzed select a patient dosage plan that is stored on a database. An example of such an analysis can be explained using the health survey questionnaire described above. For instance, if the PHQ—2 score (see FIG. 2H) is greater than or equal to 3 on an average of over 21 days, which indicates high feelings of depression, the system increases the dosing pattern (e.g., increase the pattern towards A1 from FIG. 4A). If the PHQ—2 score (see FIG. 2H) is less than 3 on an average of over 21 days the system maintains the dosing pattern (e.g., the patient is instructed to follow the same pattern from FIG. 4A). If the adverse effects score (see FIG. 2G) increases, the system will again select a dosage plan with a reduced dose amount or will select other dosing plans that spread the dose amounts over larger intervals. Ultimately, the selected dosing plan is provided to the patient via the electronic interface.

The following discussion involves an application of the methods described herein as applied to an FDA approved moderate marketed therapeutic doses of phentermine in the United States, which extended the efficacy of the drug in individuals. The doses are 37.5 mg and 15 mg per capsule. As used herein, the term low dose can mean any subtherapeutic dose of a drug which would have little or no clinical effect if given continuously and/or is typically below the FDA minimum recommended dose, including a very low dose such as less than 4 mg, less 2 mg, less than 1 mg, or 0 mg. Further, the moderate dose can include 5 mg-50 mg, such as 7.5 mg-35 mg of phentermine. The moderate dose in each weekly supply can include at least 5 mg, at least 7.5 mg more, or at least 10 mg more phentermine than the low dose.

The dose patterns can include a variation of moderate and low doses. For example, in a one-week regimen, at least 25% or at least 30% of the prescribed doses can be low doses. If a single dose is given each day for a week, at least one, at least two, or at least three of the seven doses can be the low dose. Further, at least one dose, at least two doses, or at least three doses in the one-day for a week regimen can be the moderate dose. Two exemplary sets of dose regimens of phentermine are shown in FIGS. 6A and 6B. Referring to FIG. 6, the various regimen options can vary from pattern level 1 with the least amount of medication (all low doses) up to pattern 6 with the greatest amount of medication (four moderate doses of 35 mg each). Likewise, referring to FIG. 6B, the various regiment options can vary from pattern level A with the least amount of medication up to pattern F with the greatest amount of medication. In some embodiments, 30%-90% of the doses in a single week can be low doses.

In some embodiments, additional dose regimens can be provided to the patient based upon feedback or measurements taken from the patient after the patient has been administered a first dose regimen. For example, the patient's hunger level and/or level of side effects and/or weight can be used to determine the patient's next dose regimen. A patient's exercise level and/or amount of sleep can also be used as an input to determine the proper dose pattern level.

Figure 5B:
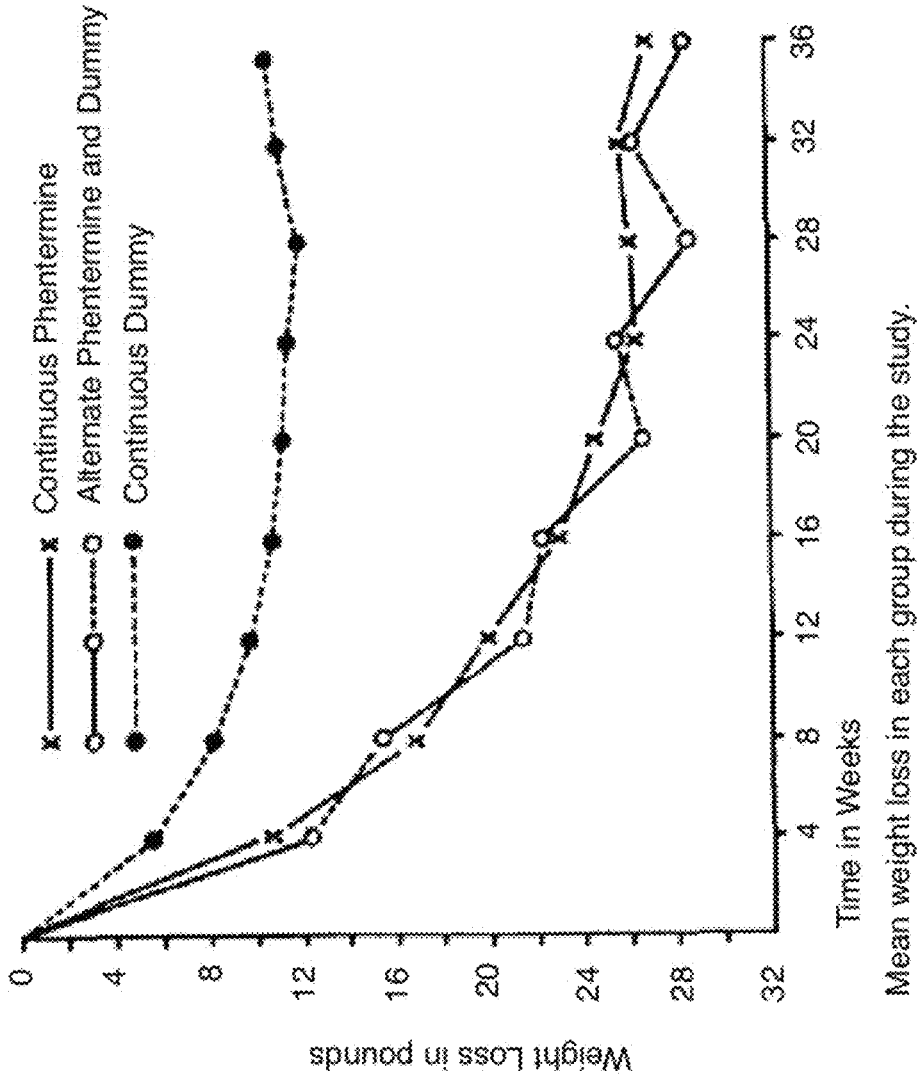
FIG. 5B is a comparison graph showing weight loss of patients in various previously published clinical trials using phentermine.

FIGS. 5A and 5B shows the results of various published clinical studies of phentermine.

Studies using phentermine alone or phentermine mixed with a placebo have reported significant patient dropout rates in a typical 8-12 weeks phentermine clinical trial (Lucey et al "Chlorphentermine, A New 'Appetite Suppressant,' A Cross-Over Double-Blind Trial," Ulster Med. J., 1962, pages 181-184 reports a 66% dropout rate, Kim et al., "Effects on Weight Reduction and Safety of Short-Term Phentermine Administration in Korean Obese People," Yonsei Med J., 2006 Vol. 47, No. 5, pages 614-625 reports a 47% dropout rate, Truant reports a 66% dropout rate, Munro reports a 41% dropout rate, and Langlois et al., "A Double-Blind Clinical Evaluation of the Safety and Efficacy of Phentermine Hydrochloride (Fastin) in the Treatment of Exogenous Obesity," Curr Ther Res Clin Exp., 1974, Vol. 16, No. 4, pages 289-296 reports a 41% dropout rate). For broad clinical adoption, the intent to treat weight loss, e.g., the average weight loss of all the patients that were enrolled in the study, is the key measure. Referring to Table 1A, the intent to treat weight loss would be reduced to 9.0 lb for the patients receiving phentermine and 3.5 lb for those on placebo if the individuals who dropped out and did not lose any net weight were included in the results.

As a result of the drawbacks associated with phentermine, clinicians are reluctant to prescribe the drug for these reasons. For example, in the United States in 1992, less than 500,000 phentermine prescriptions were dispensed even though there were 60,000,000 people in the U.S. in need of medical therapy for obesity. However, phentermine remains a promising medication for inducing weight lots if used under the systems and methods described herein.

An exemplary method for treating a patient with phentermine to induce weight loss can thus include:
(i) Weighing the patient;
(ii) Administering one pill a day of either a moderate dose of phentermine or a low dose of phentermine for a week in one of several weekly dose patterns, such as the patterns described in FIG. 6A;
(iii) Weighing the patient during or after the weekly regimen and/or monitoring the patient's hunger and/or side effects; and
(iv) Based on the weight change, hunger level, and/or side effects reported, adjusting the dose pattern level taken for the next week; and
(v) Repeating steps (i-iv) until the patient loses their target excess body weight.

The type of dose regimen (e.g., dose patterns levels 1 to 6 in FIG. 6A or pattern levels A-F in FIG. 6B) can be selected for a patient for a given time period (e.g., week) using an algorithm that is designed to minimize patient exposure to the drug, minimize side effects, and induce the desired weight loss. For example, in one embodiment, if significant side effects are reported, then the dose pattern level can be reduced. If hunger persists, but little to no side effects are reported, then the dose pattern level can be increased. If the weight is not reducing by a goal amount (e.g., 1 lb/week, 1.51 bs/week, 2 lbs/week), then the dose pattern level can be increased. If the weight is reducing by the goal amount per week, then the dose pattern level can be kept constant. In some embodiments, a patient can receive less than 50%, such as less than 40% or approximately 25% of the amount of medication using this algorithm that he or she would have on a standard continuous dose.

Figure 7:
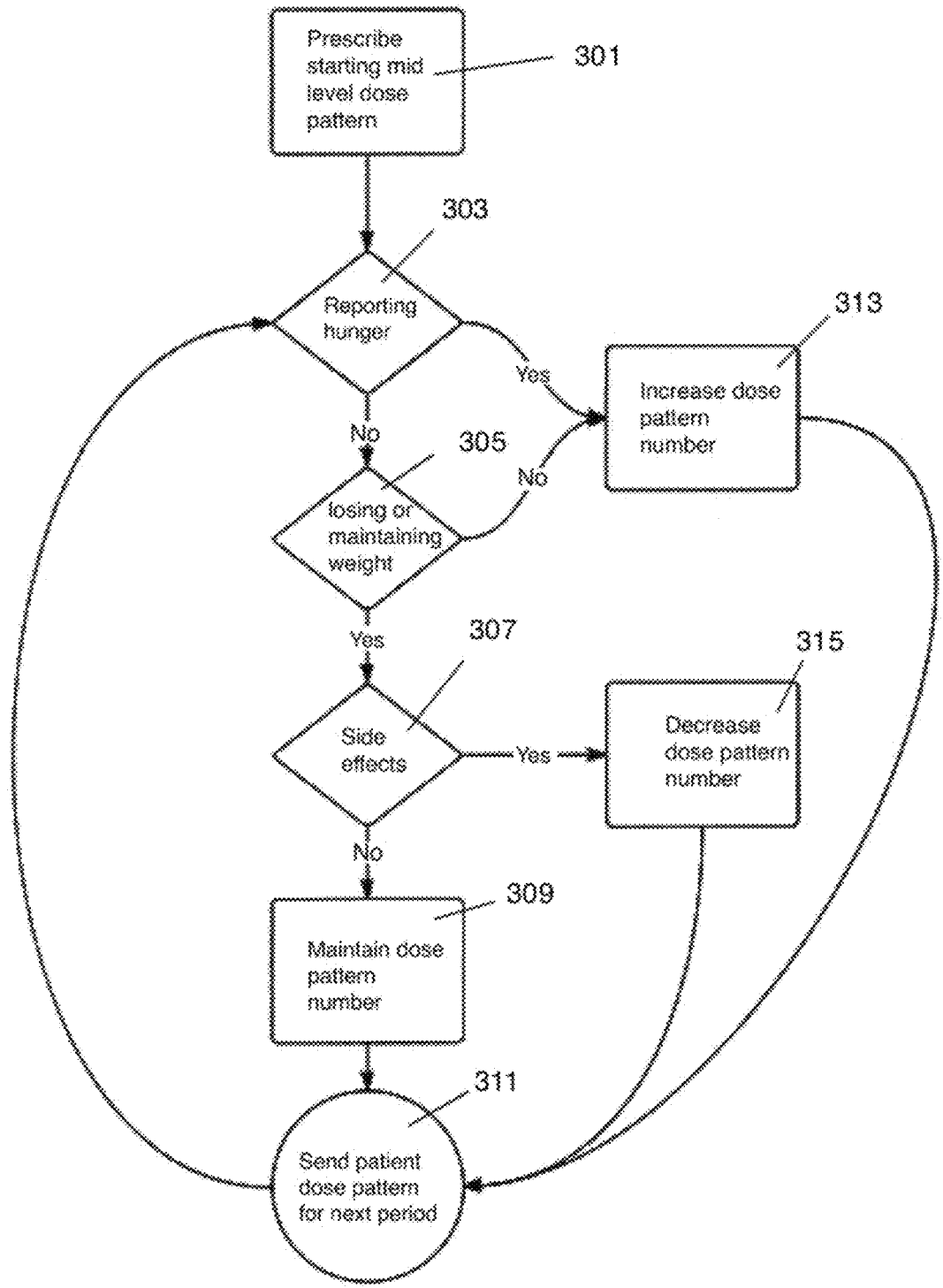
FIG. 7 is a flow chart showing an exemplary method of inducing weight loss by varying dosages of phentermine as described herein.

An exemplary method 300 of treating a patient using such an algorithm is shown in FIG. 7. At step 301, a prescribed dose pattern is given to the patient. At step 303, the patient reports his or her hunger. If the patient reports increased or standard hunger levels, then the overall dose or dose pattern level is increased at step 313. On the other hand, if the patient reports decreased hunger levels, then it can be determined at step 305 whether the patent is losing or maintaining weight. If not, then at step 313, the dose or dose pattern level is increased. However, if the patient has lost weight, then it can be determined if there are substantial side effects associated with the dose at step 307. If there are substantial side effects, then the dose or dose pattern level can be decreased. If there are no substantial side effects, then the dose pattern level can be maintained at step 309. Once the next dosage has been determined (either at steps 313, 315, or 309), then the new dose pattern can be provided to the patient at step 311. The method 300 can be performed at any desired time. For example, the method might be performed one a week, once every two weeks, once a month, or even once every day or two.

Figure 8:
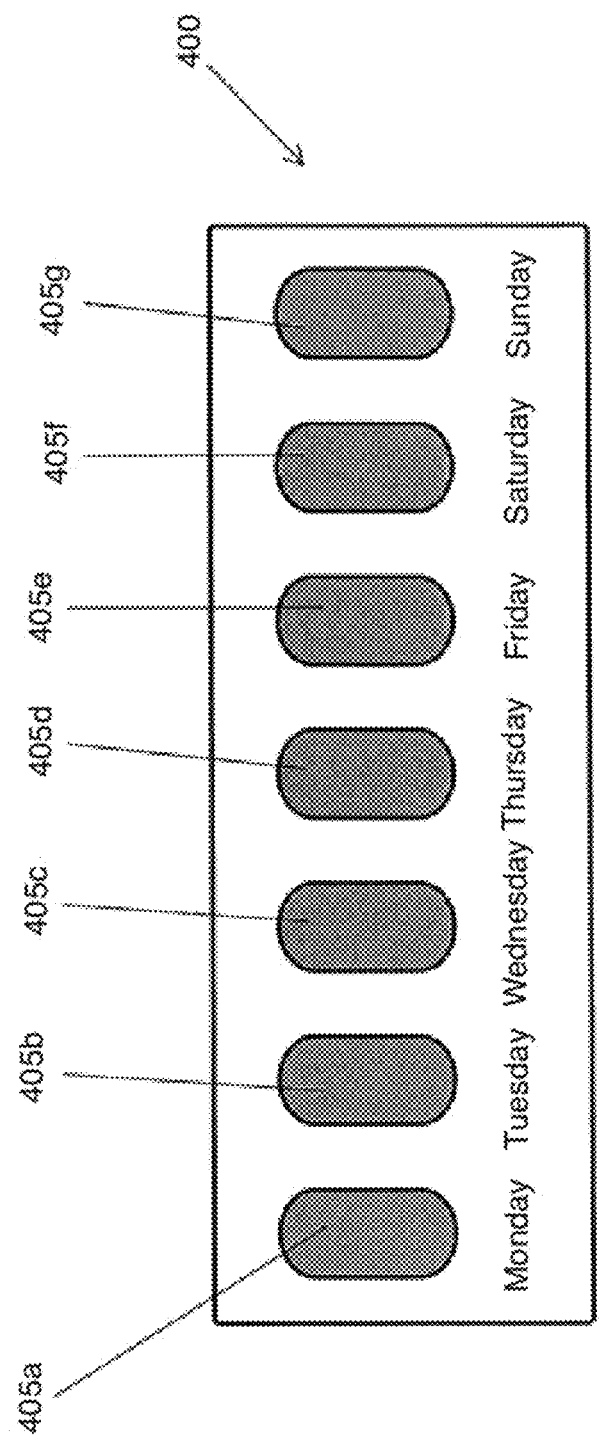
FIG. 8 shows an exemplary weekly pack of medication dose units as described herein.

In some embodiments, referring to FIG. 8, the sets of dose regimens can be provided to the patient in a single pack, such as a blister pack. For example, there can be seven dose units 405a-g (e.g., pills, capsules, or vials) that appear identical (i.e., the user cannot tell the difference between the different dose amounts) in a single pack 400. Because the dose units 105a-g appear identical, but actually may include different doses of medication (e.g., according to the dose pattern levels shown in FIGS. 6A and 6B), the various dose units can be marked to indicate when the patient should take each particular dose unit. For example, the dose units can be marked with the days of the week, as shown in FIG. 8. Alternatively or in addition, the dose units 405a-g can be numbered. The pack can include a weekly, biweekly, or monthly supply of medication.

Additional objectives, advantages, and novel features of the present invention will become apparent to one ordinarily skilled in the art upon examination of the following example, which is not intended to be limiting.

A study was performed including 23 overweight (7) and obese (16) patients whose average initial weight was 207 lb. Inclusion and exclusion criteria were similar to those of many published phentermine clinical trials. The patients were offered conventional dietary advice, provided meal replacements in the form of one to two commercial shakes (Usana Health Sciences, Salt Lake City, Utah), and were encouraged to exercise. Historical controls available from many published data about weight loss that involved dietary advice, meal replacement, and encouragement to exercise were used. An example of the results from published studies using such controls is shown in FIG. 9.

During the study, each patient was prescribed a customized dose pattern level of moderate capsules of phentermine and low dose capsules of phentermine that were provided on a biweekly basis in a 7-compartment blister pack where each blister contained a daily red capsule. The patient was instructed to take the appropriate daily capsule in the morning around breakfast time. The pack was labeled "each capsule contains up to 35 mg of phentermine." In this example, each capsule contained 35 mg, 15 mg, 10 mg, 7.5 mg or 0 mg of phentermine in addition to inert excipients. The patients received two dose pattern weekly medications strips every two weeks.

In addition to the pills, patients were given a smartphone app or access to a browser-based reporting form where they could report their daily weight, drug compliance, hunger level, exercise level, and side effects experienced. The data was fed directly to a database, which was analyzed by the physician administering the trial and his assistant.

The algorithm for treatment included the following steps:
(1) Each patient was started on a weight loss dose pattern with a midlevel weekly phentermine dose pattern level 2 as shown in FIG. 6A. Patients with concerns about high levels of sensitivity to medicines in the past were started on the lowest effective phentermine dose.
(2) The maximum tolerated weight loss dose pattern for the patient was determined by reviewing the patient's current dose level pattern and his or her electronically reported daily hunger level and side effects such as sleeplessness.
(3) If the patient had significant side effects such as insomnia or nervousness, his or her dose pattern level was reduced, for example from 3 to 2 or from 4 to 3.
(4) If the patient reported persistent hunger but no significant side effects, his or her dose pattern level was increased, for example from 3 to 4 or from 4 to 5.
(5) If the patient's weight was dropping at least 1.5 lbs/week or 6 lbs/month, his or her dose pattern level was kept constant until they achieved their target weight.
(6) If the patient's weight failed to drop by at least 1 lbs/week or 6 lbs/month and hunger was limiting their progress, his or her dose pattern was increased for the subsequent week unless limited by adverse effects or sensitivity to medicine.
(7) Once the patient achieved his or her target, the patient was put on a maintenance dose level patterns comprising of the lowest dose level pattern used in their treatment.
(8) After 12 weeks of the maintenance dose pattern level, patients were generally adjusted to the lowest dose pattern level. If a patient started to gain weight while on the maintenance dose pattern level, it was increased for the subsequent period, for example from 1 to 2 or 2 to 3, etc., and the process was restarted at step 5 or 6.
(9) All therapy was discontinued after 9 months or earlier if the patient displayed stable weight for more than 3 months and reported no hunger issues.

Figure 10:
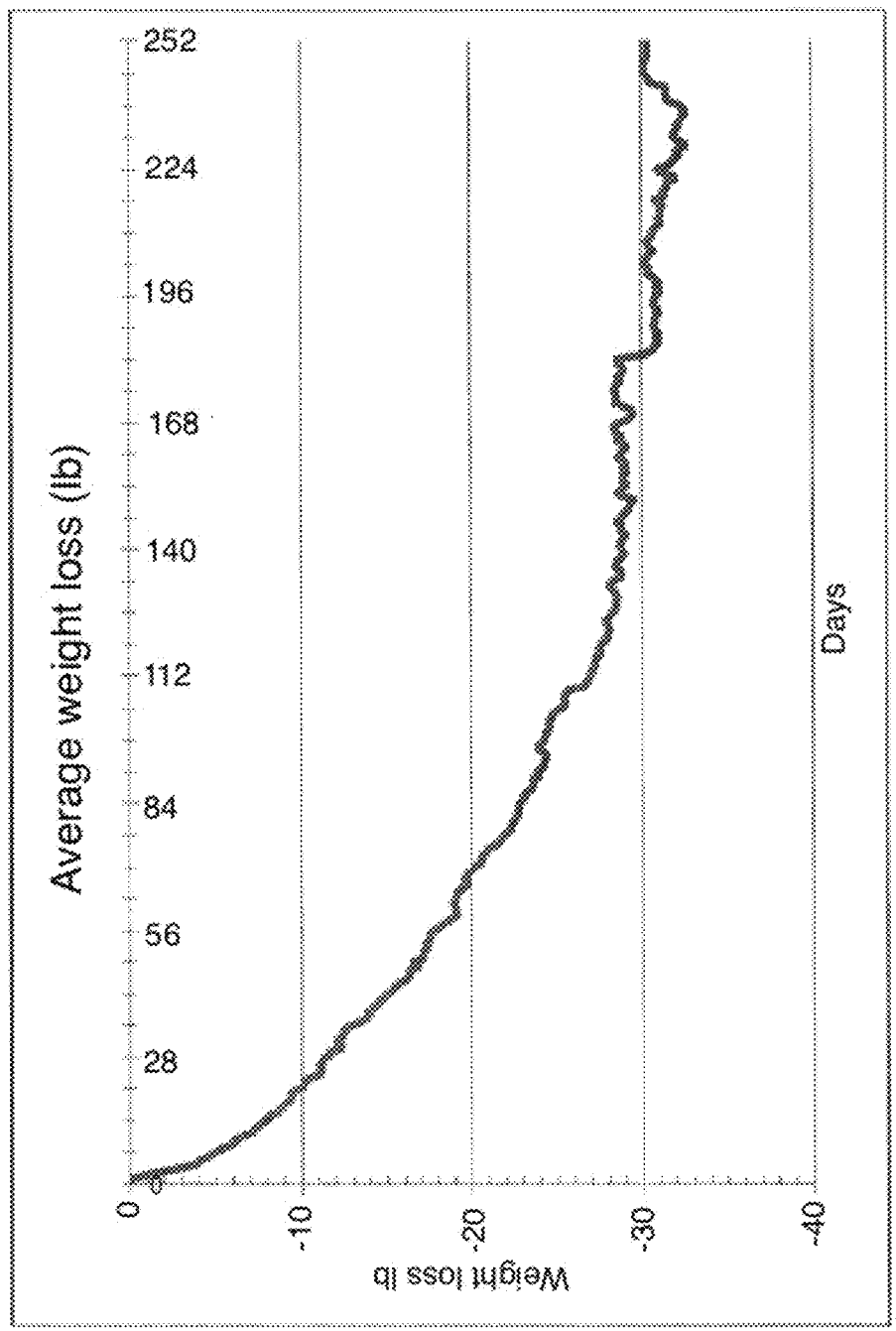
FIG. 10 is a graph showing the average weight loss of patients when varying dosages of phentermine as described herein.

A graph of the results from the study is shown in FIG. 10. Further, a comparison between the results achieved by the present study and those reported by Munro is provided in FIG. 9.

The hunger and weight responsive patient-specific regimen of the study allowed patients to achieve substantial weight loss and sustain it over long intervals exceeding average of 31 treatment weeks. The average twelve-week weight loss was 23 lb. This was achieved for the group on intent to treat basis compared with 15 lbs. reported by Munro with alternating monthly placebo/active trial (see FIG. 9).

The drug treatment was stopped when the patient indicated that they felt like they could manage hunger without the drug. The average period of drug treatment was 23 weeks. None of the patients failed to complete the first 12 weeks in the program, which indicates high level of tolerability of the regimen. Lower reported side effects rate was observed once the initial dose was titrated.

The average total drug exposure was 75% lower than a typical phentermine regimen and 50% lower than Munro monthly phentermine/placebo group. Average period of therapy was 31 weeks. The trial is ongoing, and each patient was offered to continue for 36 weeks (9 months).

Historically, about one-fourth of the patients stay at a constant weight after completing phentermine weight loss therapy that is limited to a maximum continuous effective dosing of 12 weeks by the FDA. The alternating moderate and low doses in weekly patterns described herein allows the clinician to administer a long-term drug regimen with beneficial results because the patient continues to achieve steady control of hunger without building tolerance to the drug. The data above demonstrates that patients are able to lose more weight than in previous phentermine trials and maintain that weight loss for a longer period. This increases the likelihood of permanent weight loss and long-term behavioral changes. The inventors demonstrated that the combination of phentermine with a low dose is both safe and effective as a treatment of overweight and obesity.

Although described above using treatment of weight loss with phentermine as an example, it is to be understood that other medications can be used and/or other indications can be treated using the methods, systems, and kits described herein. For example, other obesity drugs, such as a combination of phentermine and torpiramate, could be used. Alternatively, the methods and systems described herein can be used to treat attention deficit disorder (e.g., with a psychostimulant or stimulant), mental disorders, such as depression (e.g., with an anti-depressant), and/or pain (e.g., with a narcotic or neuropathic). Advantageously, the patient can provide feedback on symptoms (e.g., hyperactivity or mood) and side effects and then be provided medication in dose pattern levels as described above based upon the feedback. The dose schedule can be chosen that administers the minimum effective active dose and extends the interceding number of days that the patient receives a low dose while achieving the clinical end points. The methodologies described herein can be particularly advantageous when using medications that commonly cause adverse side effects or engenders drug tolerance when used continuously.

Although described above as modulating moderate and low doses in the dose patterns, in some embodiments, the moderate dose can be provided and then no dose unit can be provided in place of the low dose.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

I claim:

1. A method of electronically adjusting a dosing regimen of a patient undergoing a medical regimen with a medicinal substance, the method comprising:

providing an electronic interface to the patient, where the electronic interface is configured to collect a plurality of patient data from the patient in electronic form, where the plurality of patient data is associated with an effect of the medicinal substance on the patient;

collecting, from the patient, the plurality of patient data in electronic form by transmitting the plurality of patient data using the electronic interface to a server over a network;

analyzing, using one or more processors of the server, the plurality of patient data in electronic form to select a patient dosage plan from a database containing a plurality of pre-determined dosage plans stored on the server, where each pre-determined dosage plan includes a plurality of dosage amounts and a dosage cadence, where the dosage cadence of at least two pre-determined dosage plans differs wherein analyzing the plurality of patient data to select the patient dosage plan further comprises applying a machine-learning algorithm to select the patient dosage plan from the database containing a plurality of pre-determined dosage plans, wherein the machine-learning algorithm takes into account the plurality of dosage amounts and the dosage cadence from the database to select the patient dosage plan;

where the plurality of dosage amounts in at least one pre-determined dosage plan includes at least a fractional dosage amount and a full dosage amount, where the plurality of dosage amounts are individual dosage amounts each delivered in accordance with the dosage cadence; and transmitting the patient dosage plan having a patient dosage amount from the server to the electronic interface to provide the patient with access to the patient dosage plan;

where the electronic interface is configured to permit the patient to view at least a portion of the patient dosage amount on an electronic display of the electronic interface, wherein the patient dosage plan instructs the patient to follow the patient dosage plan over a period of time such that a duration of efficacy of the medicinal substance is extended.

2. The method of claim 1, wherein the electronic interface is configured to collect the plurality of patient data from a personal electronic device configured to measure biologic or behavioral data from the patient.

3. The method of claim 1, wherein the electronic interface is configured to collect the plurality of patient data from a personal electronic device configured to produce the plurality of patient data from a test of a biologic sample from the patient, and where analyzing the plurality of patient data comprises identifying one or more biomarkers from the biologic sample.

4. The method of claim 1, wherein the electronic interface is configured to present to the patient a health survey having at least one health survey questionnaire, wherein the electronic interface is further configured to compile the plurality of patient data from a response of the patient to the at least one health survey questionnaire, where the at least one health survey questionnaire includes a plurality of survey questions regarding the effect of the medicinal substance on the patient.

5. The method of claim 4, wherein the plurality of survey questions regarding the effect of the medicinal substance on the patient includes at least one survey question related to an effectiveness of the medicinal substance on the patient.

6. The method of claim 4, wherein the plurality of survey questions regarding the effect of the medicinal substance on the patient includes at least one survey question related to a change in behavioral practices of the patient during the period of time.

7. The method of claim 1, wherein providing the electronic interface to the patient occurs after a first period of time during which the patient follows an existing dosing plan for the medicinal substance, the existing dosing plan having an existing dosage amounts and an existing dosing cadence.

8. The method of claim 7, wherein a dosage cadence of the patient dosage plan differs from a dosage cadence of the existing dosing plan.

9. The method of claim 7, wherein the plurality of dosage amounts in the patient dosage plan differs from the existing dosage amounts.

10. The method of claim 1, wherein the plurality of dosage amounts further includes a zero dosage amount.

11. The method of claim 1, further comprising providing the patient with a plurality of doses of the medicinal substance in an amount equal to the patient dosage amount.

12. The method of claim 11, wherein each of the plurality of doses of the medicinal substance appear identical.

13. The method of claim 1, wherein the patient dosage amount is obscured from the patient.

14. The method of claim 1, wherein the patient dosage plan is a same as a previously existing dosing plan.

15. The method of claim 1, wherein the plurality of dosage amounts comprises at least one dosage amount below a level to produce a clinical effect.

16. The method of claim 1, wherein transmitting the plurality of patient data to the server occurs daily.

17. The method of claim 1, wherein transmitting the plurality of patient data to the server occurs weekly.

18. The method of claim 1, where each pre-determined dosage plan in the plurality of pre-determined dosage plans is unique.

19. A method of electronically adjusting a dosing regimen of a patient undergoing treatment for weight loss with phentermine, the method comprising:

providing an electronic interface to the patient, where the electronic interface is configured to collect a plurality of patient data in electronic form, where the plurality of patient data is associated with an effect of the phentermine on the patient;

collecting, from the patient, the plurality of patient data in electronic form by transmitting the plurality of patient data using the electronic interface to a server over a network;

analyzing, using one or more processors of the server, the plurality of patient data in electronic form to select a patient dosage plan from a database containing a plurality of pre-determined dosage plans stored on the server, where each pre-determined dosage plan includes a plurality of dosage amounts and a dosage cadence;

where the plurality of dosage amounts in at least one pre-determined dosage plan comprise phentermine and includes at least a fractional dosage amount and a full dosage amount, where the plurality of dosage amounts are individual dosage amounts each delivered in accordance with the dosage cadence; and transmitting the patient dosage plan having a patient dosage amount from the server to the electronic interface to provide the patient with access to the patient dosage plan;

where the electronic interface is configured to permit the patient to view at least a portion of the patient dosage amount on an electronic display of the electronic interface, wherein the patient dosage plan instructs the patient to follow the patient dosage plan over a period of time.

20. The method of claim 1, where the plurality of dosage amounts in at least two pre-determined dosage plans includes at least a fractional dosage amount and a full dosage amount.

\* \* \* \* \*